(12) United States Patent
Tornier et al.

(10) Patent No.: US 7,476,227 B2
(45) Date of Patent: Jan. 13, 2009

(54) TOOL FOR PLACING A MALLEOLAR IMPLANT FOR PARTIAL OR TOTAL ANKLE PROSTHESIS

(75) Inventors: Alain Tornier, Saint Ismier (FR); Michel Bonnin, Francheville (FR); Jean-Alain Colombier, Balma (FR); Thierry Judet, Ville d'Avray (FR)

(73) Assignee: Tornier SAS, Saint Ismier (FR)

( * ) Notice: Subject to any disclaimer, the term of this patent is extended or adjusted under 35 U.S.C. 154(b) by 561 days.

(21) Appl. No.: 10/254,984

(22) Filed: Sep. 26, 2002

(65) Prior Publication Data

US 2003/0028198 A1    Feb. 6, 2003

Related U.S. Application Data

(62) Division of application No. 09/631,938, filed on Aug. 3, 2000, now Pat. No. 6,488,712.

(30) Foreign Application Priority Data

Aug. 5, 1999    (FR)    .................................. 99 10340

(51) Int. Cl.
*A61B 17/58*    (2006.01)
(52) U.S. Cl. .................. 606/96; 606/99; 623/21.18
(58) Field of Classification Search ............. 606/96–98, 606/79, 80; 623/21.11, 21.18
See application file for complete search history.

(56) References Cited

U.S. PATENT DOCUMENTS

| | | | | |
|---|---|---|---|---|
| 2,393,831 A | * | 1/1946 | Stader | 606/56 |
| 3,987,500 A | * | 10/1976 | Schlein | 623/21.18 |
| 4,232,404 A | * | 11/1980 | Samuelson et al. | 623/21.18 |
| 4,235,428 A | | 11/1980 | Davis | |
| 4,257,411 A | * | 3/1981 | Cho | 606/96 |
| 4,644,943 A | * | 2/1987 | Thompson et al. | 606/64 |
| 4,722,331 A | * | 2/1988 | Fox | 606/96 |
| 4,862,882 A | * | 9/1989 | Venturi et al. | 606/96 |
| 5,171,289 A | | 12/1992 | Tornier | |
| 5,312,409 A | * | 5/1994 | McLaughlin et al. | 606/86 |
| 5,314,485 A | | 5/1994 | Judet | |
| 5,326,359 A | | 7/1994 | Oudard | |
| 5,358,526 A | | 10/1994 | Tornier | |
| 5,383,937 A | * | 1/1995 | Mikhail | 623/20 |
| 5,403,321 A | * | 4/1995 | DiMarco | 606/96 |
| 5,405,399 A | | 4/1995 | Tornier | |
| 5,429,639 A | | 7/1995 | Judet | |

(Continued)

OTHER PUBLICATIONS

Rochetin, U.S. Appl. No. 11/194,452, entitled "Patellar Retractor and Method of Surgical Procedure on Knee," filed Aug. 2, 2005.

(Continued)

*Primary Examiner*—Eduardo C Robert
*Assistant Examiner*—Mary Hoffman
(74) *Attorney, Agent, or Firm*—Faegre & Benson LLP

(57) ABSTRACT

A tool for placing a malleolar implant for partial or total ankle prosthesis, which includes a spacer block, adapted to be inserted between a tibia and an astragalus of an ankle, a lug secured to the block and extending to a vicinity of an outer surface of a fibular malleolus when the spacer block is in position, and the lug supporting a guide for boring the malleolus from its outer surface.

23 Claims, 4 Drawing Sheets

U.S. PATENT DOCUMENTS

| | | | |
|---|---|---|---|
| 5,458,650 A | 10/1995 | Carrett et al. | |
| 5,505,731 A | 4/1996 | Tornier | |
| 5,591,168 A | 1/1997 | Judet et al. | |
| 5,662,651 A | 9/1997 | Tornier et al. | |
| 5,674,224 A * | 10/1997 | Howell et al. | 606/88 |
| 5,676,702 A | 10/1997 | Ratron | |
| 5,690,676 A * | 11/1997 | DiPoto et al. | 606/232 |
| 5,702,447 A | 12/1997 | Walch et al. | |
| 5,702,457 A | 12/1997 | Walch et al. | |
| 5,702,478 A | 12/1997 | Tornier | |
| 5,766,256 A | 6/1998 | Oudard et al. | |
| 5,766,259 A * | 6/1998 | Sammarco | 623/21.18 |
| 5,824,106 A | 10/1998 | Fournol | |
| 5,879,395 A | 3/1999 | Tornier et al. | |
| 5,931,837 A * | 8/1999 | Marsh et al. | 606/55 |
| 6,136,032 A * | 10/2000 | Viladot Perice et al. | 623/21.18 |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 * | 2/2001 | Bonnin et al. | 623/21.18 |
| 6,206,925 B1 | 3/2001 | Tornier | |
| 6,299,646 B1 | 10/2001 | Chambat et al. | |
| 6,328,758 B1 | 12/2001 | Tornier et al. | |
| 6,334,874 B1 | 1/2002 | Tornier et al. | |
| 6,379,387 B1 | 4/2002 | Tornier | |
| 6,454,809 B1 | 9/2002 | Tornier | |
| 6,488,712 B1 | 12/2002 | Tornier et al. | |
| 6,540,770 B1 | 4/2003 | Tornier et al. | |
| 6,582,469 B1 | 6/2003 | Tornier | |
| 6,599,295 B1 | 7/2003 | Tornier et al. | |
| 6,626,946 B1 | 9/2003 | Walch et al. | |
| 6,761,740 B2 | 7/2004 | Tornier | |
| 6,767,368 B2 | 7/2004 | Tornier | |
| 6,802,864 B2 | 10/2004 | Tornier | |
| 6,824,567 B2 | 11/2004 | Tornier et al. | |
| 6,890,357 B2 | 5/2005 | Tornier | |
| 6,969,406 B2 | 11/2005 | Tornier | |
| 7,033,396 B2 | 4/2006 | Tornier | |
| 2003/0009170 A1 | 1/2003 | Tornier | |
| 2003/0009171 A1 | 1/2003 | Tornier | |
| 2004/0134821 A1 | 7/2004 | Tornier | |
| 2004/0210220 A1 | 10/2004 | Tornier | |
| 2004/0215200 A1 | 10/2004 | Tornier | |
| 2004/0230197 A1 | 11/2004 | Tornier et al. | |
| 2005/0049709 A1 | 3/2005 | Tornier | |
| 2005/0055102 A1 | 3/2005 | Tornier et al. | |
| 2005/0165490 A1 | 7/2005 | Tornier | |
| 2005/0203536 A1 | 9/2005 | Laffargue et al. | |
| 2005/0278030 A1 | 12/2005 | Tornier et al. | |
| 2005/0278031 A1 | 12/2005 | Tornier et al. | |
| 2005/0278032 A1 | 12/2005 | Tornier et al. | |
| 2005/0278033 A1 | 12/2005 | Tornier et al. | |
| 2005/0288791 A1 | 12/2005 | Tornier et al. | |
| 2006/0015185 A1 | 1/2006 | Chambat et al. | |
| 2006/0173457 A1 | 8/2006 | Tornier | |
| 2006/0235538 A1 | 10/2006 | Rochetin et al. | |

OTHER PUBLICATIONS

Rochetin et al., U.S. Appl. No. 11/401,415, entitled "Surgical Apparatus for Implantation of a Partial or Total," filed Apr. 11, 2006.

Rochetin, U.S. Appl. No. 11/670,274, entitled "Offset Stem Tibial Implantation," filed Feb. 1, 2007.

Ratron et al., U.S. Appl. No. 11/626,735, entitled "Surgical Instrumentation Kit for Inserting an Ankle Prosthesis," filed Jan. 1, 2007.

* cited by examiner

TOOL FOR PLACING A MALLEOLAR IMPLANT FOR PARTIAL OR TOTAL ANKLE PROSTHESIS

CROSS REFERENCE TO RELATED APPLICATIONS

This application is a divisional application of Ser. No. 09/631,938 filed Aug. 3, 2000 now U.S. Pat. No. 6,488,712 and claiming priority from French application Serial Number 99 10340 filed Aug. 5, 1999.

BACKGROUND OF THE INVENTION

1. Field of the Invention

The present invention relates to a malleolar implant for a partial or total prosthesis of the ankle and to an ancillary tool for placing such an implant.

2. Brief Description of the Related Art

It is known, for example from EP-A-O 864 304, to fit an ankle prosthesis with a malleolar implant that bears against an articular surface of the astragalus, whether it be a natural surface or of a surface of a prosthetic component. During an operation on an ankle, access to the internal articular surfaces is limited by the ligamentary system that does not necessarily allow a sufficient dislocation of the joint. In particular, access to the internal surface of the fibular malleolus may be insufficient, which induces difficulties in positioning the implant, particularly by impaction.

With reference to the embodiments of FIGS. 4 and 5, it is disclosed in EP-A-O 864 304 to introduce an implant from the outer face of the fibula. However, this necessarily limits the surface of the head of this implant, which must be less than or equal to the surface of the orifice provided in the bone, so that it is necessarily of relatively small dimensions with the result that the malleolus is fragile.

For the foregoing reasons, the positioning of the malleolar implants in the known prostheses is not entirely satisfactory.

SUMMARY OF THE INVENTION

It is a particular object of the present invention to overcome these drawbacks by proposing a novel malleolar implant which may be positioned precisely, even though access to the internal surface of the fibular malleolus may be limited and whereas its articular head presents dimensions allowing it to perform its function efficiently.

To that end, the invention relates to a malleolar implant comprising a head, that bears against the astragalus or an astragalian prosthetic component and a shank provided to be introduced in a bore in the fibula, characterized in that this shank is provided with means for hooking a traction member adapted to be manipulated from the outer side of the fibula, in order to position the shank in the bore.

Thanks to the invention, the implant may be pre-positioned towards the inner face of the fibular malleolus and pulled through the through bore provided in the malleolus, with the result that the surgeon does not have to manipulate the implant with precision inside the joint, i.e. between the fibula and the tibia or between the fibula and the astragalus. The surgeon may exert an efficient effort on the traction member, which may be a flexible tie such as a suture thread, without being hindered by the surrounding bones. As a result, the positioning of the shank of the implant in the bore in the fibula may be precise, in particular due to the fact that the outer diameter of the shank may be substantially equal to the inner diameter of this bore, as the effort of traction which may be exerted from the outside of the fibula may be intense.

According to an advantageous aspect of the invention, the shank is provided with at least one orifice for passage of a flexible tie adapted to be engaged through the bore. In particular, the shank may comprise a plurality of orifices for passage of a flexible tie, such orifices being distributed over the length of this shank.

According to another advantageous aspect of the invention, the shank is provided with means for axial hold inside the bore. These means, which may be formed by outer radial flanges distributed over the length of the shank, make it possible efficiently to immobilize the shank inside the bore after it has been introduced therein by traction on the flexible member or tie.

The invention also relates to an ancillary tool for placing a malleolar implant as described hereinabove and, more specifically, a tool which comprises a spacer block adapted to be inserted between the tibia and the astragalus of an ankle, and a lug extending from one end connected to this spacer block to an opposite end that is oriented in a vicinity of the lateral surface of the fibular malleolus when the spacer block is in place between the tibia and the astragalus, this lug supporting a guide for boring the fibular malleolus in a medio-lateral direction.

Thanks to the invention, the bore of the fibular malleolus may be effected from its outer surface and in the direction of its inner surface, with a determined relative positioning with respect to the tibia and the astragalus, with the result that the position of the malleolar implant in place in this bore is determined with precision with respect to the respective articular surfaces of the astragalus or of the tibia or of corresponding prosthetic components. The spacer block may be provided to cooperate with natural articular surfaces of the tibia and/or of the astragalus or with surfaces created by resection of these bones, in the case of placing a total ankle prosthesis.

According to an advantageous aspect of the invention, the spacer block is provided with a housing for receiving a shim of thickness adapted to the distance between the lower surface of the tibia and upper surface of the astragalus. This aspect of the invention makes it possible to maintain a distance corresponding to that which will be subsequently created by the prosthetic elements mounted in the lower part of the tibia and in the upper part of the astragalus, when the position of the malleolar implant is determined.

According to another advantageous aspect of the invention, the lug is articulated on the spacer block, with a limited possibility of pivoting. This makes it possible to adjust the position of the malleolus bore guide about the pivot axis of the lug with respect to the spacer block. In that case the spacer block and the lug are advantageously provided with orifices for passage of a common pivot pin.

It is also possible for the bore guide to be associated with a device for clamping the malleolus against a bearing surface formed on the lug or the spacer block. This allows a firm immobilization of the fibular malleolus during boring and thus ensures precision of the boring operation.

BRIEF DESCRIPTION OF THE DRAWINGS

The invention will be more readily understood on reading the following description of an embodiment of a malleolar implant and its ancillary tool according to the invention, given solely by way of example and with reference to the accompanying drawings, in which.

DESCRIPTION OF PREFERRED EMBODIMENT

Figure 1:
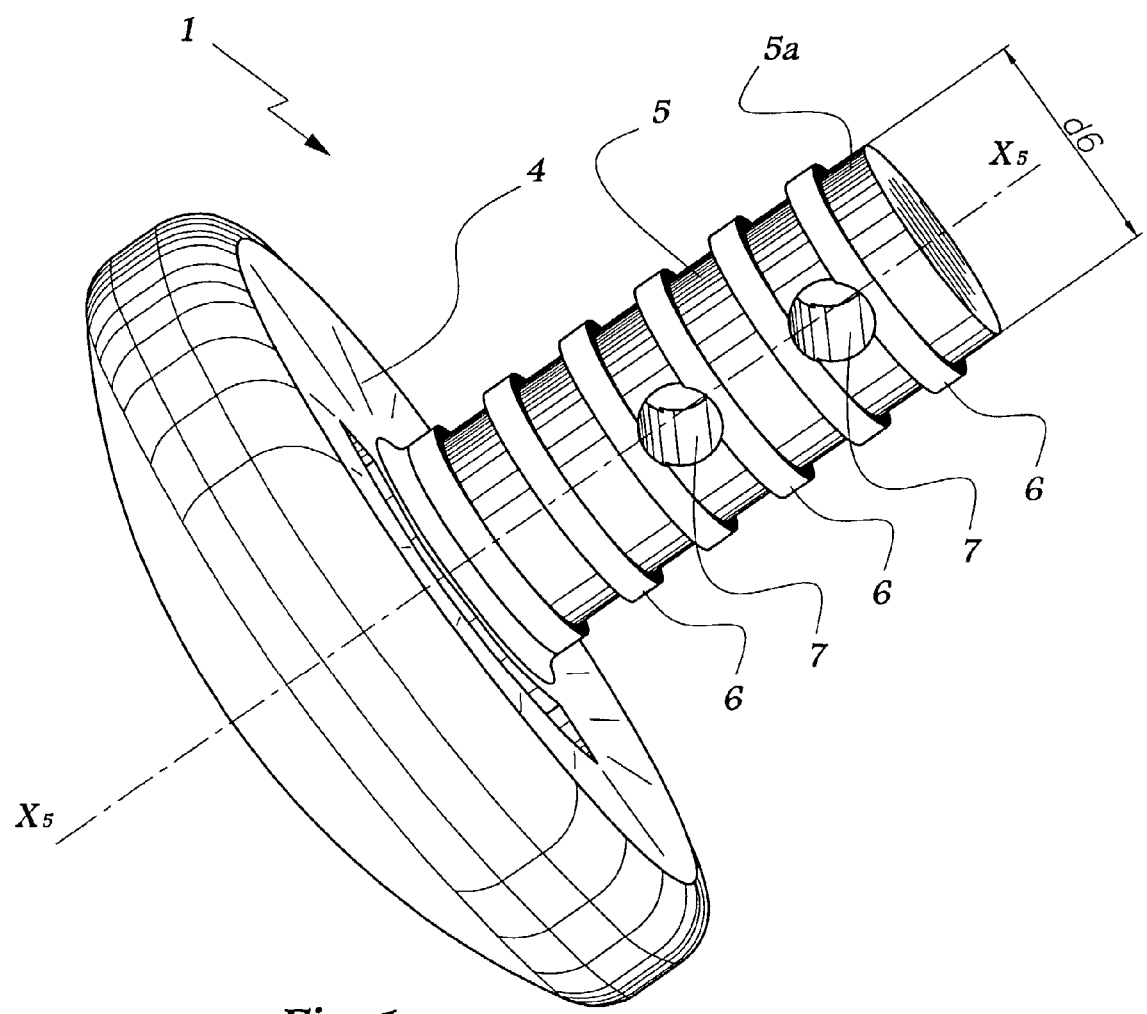
FIG. 1 is a view in perspective of an implant according to the invention.
Figure 2:
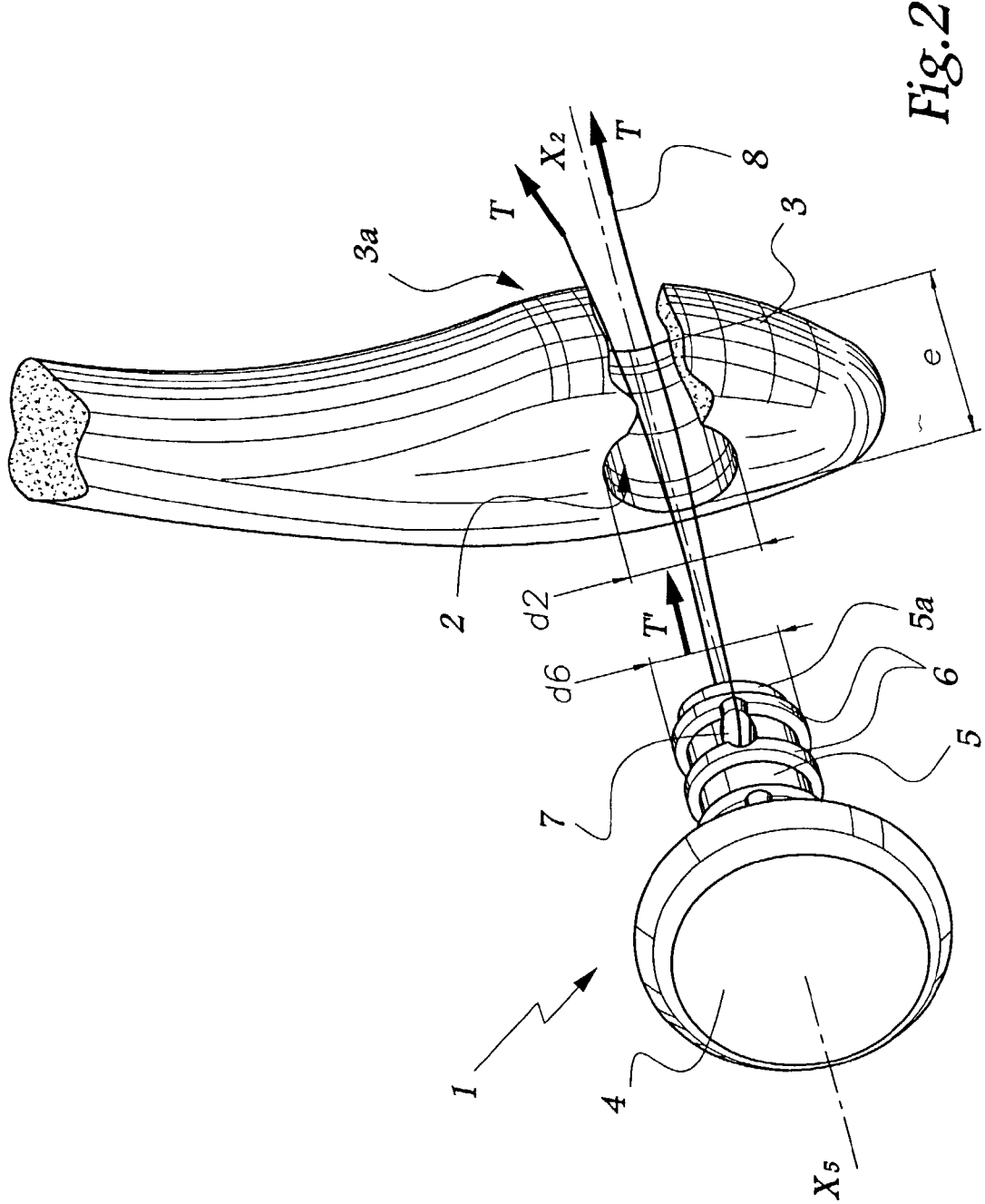
FIG. 2 is a view in perspective of the implant of FIG. 1 during positioning in a fibular malleolus, shown with parts torn away.

Referring now to the drawings, the implant 1 shown in FIGS. 1 and 2 is intended to be introduced in a bore 2 made in the lateral or fibular malleolus 3. The implant 1 comprises a convex head 4, substantially in the form of a spherical cap and of which the radius of curvature is substantially equal to that of the outer cheek of the astragalus of the ankle in question. The shank 5 of the implant 1 is provided with outer radial flanges 6 of which the outer diameter $d_6$ is substantially equal to the inner diameter $d_2$ of the bore 2.

According to the invention, two orifices 7 are provided in the shank 5 and are capable of receiving a suture thread 8 or other flexible tie. When such a thread is engaged in one of the orifices 7, it is possible to exert on the thread 8 an effort of traction T which is transmitted by the thread 8 to the shank 5 as represented by arrow T' in FIG. 2. In this way, by pulling on the thread 8, the surgeon introduces the shank 5 in the bore 2 without having to exert an effort of thrust on the head 4 which may be difficult to access due to the surrounding ligamentary system.

In other words, it suffices for the surgeon to place a thread in one of the orifices 7, to pass the two strands of the thread 8 in the bore 2 via the inner face of the malleolus, then to pull the strands via the outer side of the malleolus. The traction on the thread 8 has the effect of introducing the shank 5 of the implant 1 in the bore 2 and of applying the head 4 on the bone. The effort of traction T exerted on the thread 8 may be intense and directed parallel to the longitudinal axis $X_2$ of the bore 2, with the result that the shank is efficiently drawn towards the inside of the bore 2. In particular, taking into account the direction and intensity of the effort of traction T, the diameters $d_2$ and $d_6$ can be provided to be substantially equal, with the result that the shank 5 is firmly maintained in place after having been positioned.

The shank 5 is provided with two bores 7 distributed along its axis $X_5$, the bore 7 nearest the end 5a of the shank 5 being used. The fact that the shank 5 comprises a plurality of orifices 7 makes it possible to use an orifice 7 relatively close to the end 5a of the shank 5 and to avail of such an orifice including when the shank 5 is cut in order to adapt its length to the thickness e of the malleolus 3. The number of bores 7 may, of course, be increased if necessary.

Figure 3:
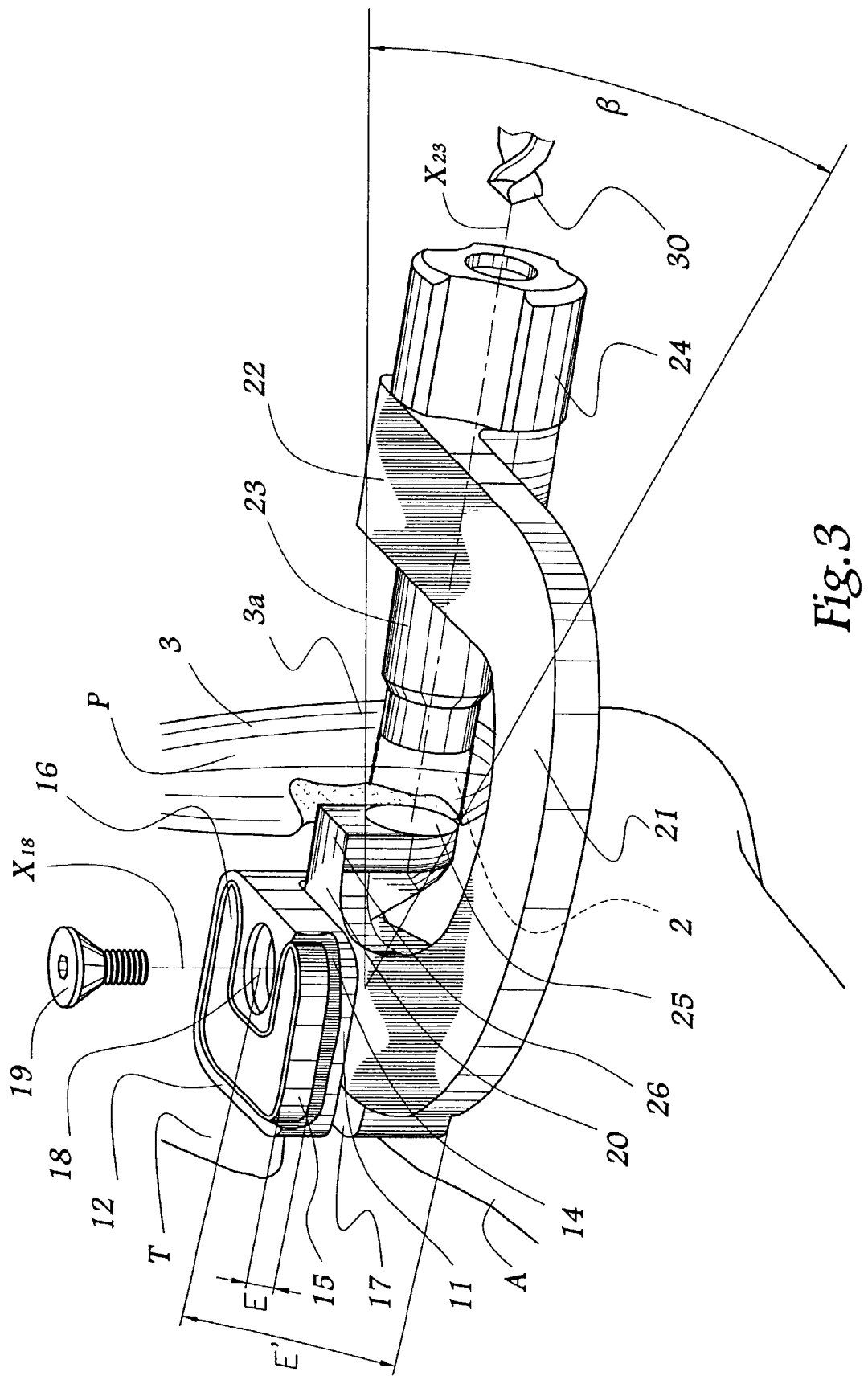
FIG. 3 schematically shows, with parts torn away, an ancillary tool for placing the implant of FIG. 1, in the course of use.
Figure 4:
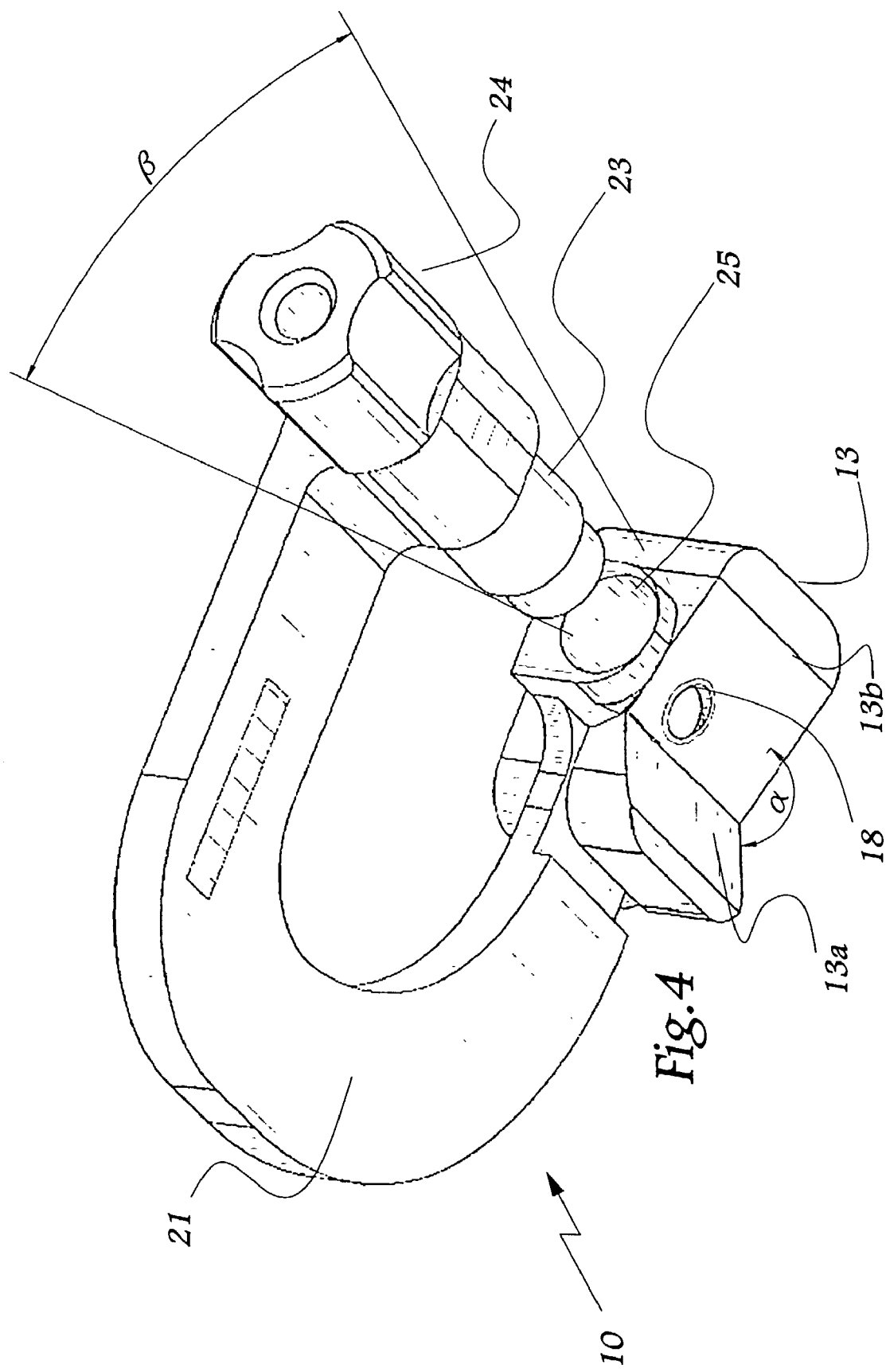
FIG. 4 is a view in perspective of the tool of FIG. 3, from underneath.

The bore 2 is made via the outer face 3a of the malleolus 3 with the aid of the ancillary tool shown in FIGS. 3 and 4. This tool 10 comprises a spacer block 11 provided to be disposed between the tibia T and the astragalus A of an ankle to be fitted with the implant 1. The block 11 comprises a substantially planar upper surface 12 intended to cooperate with a planar surface created by resection of the distal end of the tibia. The lower surface 13 of the block 11 is formed by two planar surfaces 13a and 13b inclined with respect to each other by an angle α, the surfaces 13a and 13b being provided to bear respectively on corresponding surfaces created by resection of the upper face of the astragalus A.

The surface 12 of the block 11 comprises a C-shaped housing 14 intended to receive a shim 15 of which the upper surface 16 is in contact with the lower surface of the tibia T. The thickness E of the shim 15 shown in FIG. 3 is such that its upper surface 16 is flush with the upper surface 12 of the block 11.

However, thicker shims may be used when the distance E' between the lower surface of the tibia and upper surface of the astragalus is greater than in the configuration shown in FIG. 3.

The block 11 defines a housing 17 for receiving the end 20 of a substantially C-shaped lug 21. The end 20 is provided with a bore (not shown) which, in the configuration of FIGS. 3 and 4, is aligned with a bore 18 made in the block 11 and passing downwardly through this block, i.e. connecting the surfaces 12 and 13. A screw 19 may be introduced in this bore which is at least partially tapped, this making it possible to immobilize the end 20 of the lug 21 inside the housing 17. In practice, the clearance made when the screw 19 is tightened allows a limited pivoting about axis $X_{18}$ of the bore 18.

At its end 22 opposite the end 20, the lug 21 supports a clamping system 23 adapted to be manipulated because of a knurl 24 and making it possible to apply the malleolus 3 of the fibula P against a stop 25 formed on an extension 26 of the end 20 of the lug 21. A longitudinal axis of these clamping means is shown at $X_{23}$. The clamping means 23 are hollow, with the result that a drill 30 may be introduced at the outer face 3a of the malleolus 3 in order to make the bore 2 from the outside towards the inside of the malleolus 3. In this way, the surgeon may easily aim at the suitable part of the malleolus 3 because of the clamping means 23 which also constitute a bore guide for the drill 30.

As the lug 21 is capable of pivoting about axis $X_{18}$, the position of axis $X_{23}$ is variable in pivoting about this axis $X_{18}$, which makes it possible optimally to adjust the orientation of the bore 2 as a function of the exact geometry of the malleolus 3. β denotes the maximum angle of pivoting of the axis $X_{23}$ about axis $X_{18}$. In practice, the angle β is of the order of 10°.

Thanks to the tool 10, a bore 2 may therefore be formed from the outside, allowing a rapid and efficient implantation of the implant 1.

When shims 15 of thickness greater than those shown in FIG. 2 are used, they can be provided to overlap the bore 18, as the screw 19 is placed in position before positioning of the shim 15 which is effected during operation as a function of the distance E'.

The invention has been shown with a total ankle prosthesis, which corresponds to the geometry of the surfaces 12 and 13 of the block 11. However, it is also applicable to a partial ankle prosthesis, without modification of the implant 1, the ancillary tool in that case being adapted to the geometry of the anatomical articulation surfaces between the tibia and the astragalus.

What is claimed is:

1. A kit for implanting a malleolar implant, the kit comprising:

a spacer block sized to be seated between a tibia and an astragalus of an ankle to maintain a distance between a lower surface of the tibia and an upper surface of the astragalus;

a guide adapted to locate a bore through a fibular malleolus from its outer surface, wherein the guide is pivotally adjustable with respect to the spacer block;

one shim releaseably attached to the spacer block and adapted to be located between the spacer block and one of the lower surface of the tibia or the upper surface of the astragalus;

a member connecting the spacer block to the guide, the member orienting the guide in a vicinity of the outer surface of a fibular malleolus when the spacer block is seated between the tibia and the astragalus, so that the bore positions the malleolar implant relative to the astragalus and the tibia, or prosthetic elements mounted in one or more of a lower part of the tibia and an upper part of the astragalus; and a malleolar implant comprising a head and a shank adapted to engage with the bore in a fibular malleolus, wherein the head comprises a convex front surface adapted to articulate against with one or more of the astragalus or prosthetic elements in an upper portion of the astragalus and a rear surface adapted to engage with the fibula malleolus.

2. The kit of claim 1 wherein the spacer block maintains a distance between a lower surface of the tibia and an upper surface of the astragalus generally corresponding to a separation created by prosthetic elements mounted in the lower part of the tibia and in the upper part of the astragalus.

3. The kit of claim 1 wherein the spacer block maintains a distance between a lower surface of the tibia and an upper surface of the astragalus corresponding generally to the malleolar implant bearing against the astragalus.

4. The kit of claim 1 comprising a plurality of shims at least two of which comprise different thicknesses.

5. The kit of claim 1 wherein the shim comprises an upper surface adapted to engage with the lower surface of the tibia.

6. The kit of claim 1 wherein the shim comprises an upper surface adapted to cooperate with a planar surface created by resection of a distal end of the tibia.

7. The kit of claim 1 wherein the spacer block comprises at least two lower planar surfaces.

8. The kit of claim 1 wherein the spacer block comprises surfaces adapted to cooperate with natural surfaces of at least one of the tibia and the astragalus.

9. The kit of claim 1 wherein the spacer block comprises surfaces adapted to cooperate with surfaces created by resection of at least one of the tibia and the astragalus.

10. The kit of claim 1 wherein the member and the spacer block articulate relative to each other.

11. The kit of claim 1 wherein the member is pivotally attached to the spacer block.

12. The kit of claim 1 wherein the location of the guide is adjustable with respect to the spacer block.

13. The kit of claim 1 comprising a clamping system adapted to secure the ancillary tool to the fibular malleolus.

14. The kit of claim 1 wherein the guide comprises:
a clamping device adapted to bear against the outer surface of a fibular malleolus; and
a hole in the clamping device adapted to receive a drill.

15. The kit of claim 1 wherein the guide comprises a clamping device adapted to bear against the outer surface of a fibular malleolus while at least one of the spacer block or the member bears against an opposite surface of the fibular malleolus.

16. A kit for implanting a malleolar implant, the kit comprising:
a spacer block adapted to be seated between a tibia and an astragalus of an ankle that maintains a distance between a lower surface of the tibia and an upper surface of the astragalus;
a guide adapted to position a bore through a fibular malleolus from its outer surface, wherein the guide is pivotally adjustable with respect to the spacer block; and a member connecting to the spacer block to the guide, the member positioning the guide proximate the outer surface of the a fibular malleolus when the spacer block is seated between the tibia and the astragalus, so that the bore is positioned with respect to one or more of the astragalus, the tibia, and prosthetic elements mounted in one or more of a lower part of the tibia and an upper part of the astragalus; and a malleolar implant comprising a head and a shank adapted to engage with the bore in a fibular malleolus, wherein the head comprises a front convex surface substantially in the form of a spherical cap adapted to articulate against with one or more of the astragalus or prosthetic elements in an upper portion of the astragalus and a rear surface adapted to engage with the fibula malleolus.

17. The kit of claim 16 wherein the malleolar implant comprises a member adapted to extend through the bore and apply a force from an outer side of the fibular malleolus to pull the shank into the bore.

18. The kit of claim 17 wherein the shank includes at least one orifice adapted to engage with the member.

19. The kit of claim 16 wherein the shank comprises surface features adapted to secure the malleolar implant in the bore.

20. The kit of claim 16 wherein the shank comprises a plurality of outer radial flanges.

21. A kit for implanting a malleolar implant, the kit comprising:
a spacer block sized to be seated between a tibia and an astragalus of an ankle to maintain a distance between a lower surface of the tibia and an upper surface of the astragalus;
a guide adapted to locate a bore through a fibular malleolus from its outer surface;
one shim releaseably attached to the spacer block and adapted to be located between the spacer block and one of the lower surface of the tibia or the upper surface of the astragalus;
a member connecting the spacer block to the guide, the member orienting the guide in a vicinity of the outer surface of a fibular malleolus when the spacer block is seated between the tibia and the astragalus, so that the bore positions the malleolar implant relative to the astragalus and the tibia, or prosthetic elements mounted in one or more of a lower part of the tibia and an upper part of the astragalus; and
a malleolar implant comprising a head and a shank adapted to engage with the bore in a fibular malleolus, wherein the head comprises a front convex surface adapted to articulate against with one or more of the astragalus or prosthetic elements in an upper portion of the astragalus and a rear surface adapted to engage with the fibula malleolus.

22. The kit of claim 21 comprising a plurality of shims at least two of which including a thickness selected to adjust the distance between a lower surface of the tibia and an upper surface of the astragalus.

23. The kit of claim 21 wherein the guide is pivotally adjustable with respect to the spacer block.

* * * * *